United States Patent
Zhou et al.

(10) Patent No.: US 11,312,672 B2
(45) Date of Patent: Apr. 26, 2022

(54) PROCESS FOR PREPARING FLUOROBENZENE AND CATALYST THEREFORE

(71) Applicant: Fujian Yongjing Technology Co., Ltd, Shaowu (CN)

(72) Inventors: Changyue Zhou, Shaowu (CN); Yong Wang, Shaowu (CN)

(*) Notice: Subject to any disclaimer, the term of this patent is extended or adjusted under 35 U.S.C. 154(b) by 0 days.

(21) Appl. No.: 16/923,099

(22) Filed: Jul. 8, 2020

(65) Prior Publication Data

US 2021/0061734 A1 Mar. 4, 2021

(30) Foreign Application Priority Data

Aug. 29, 2019 (DE) .................. DE102019123210.4

(51) Int. Cl.
| | |
|---|---|
| *C07C 17/20* | (2006.01) |
| *B01J 21/18* | (2006.01) |
| *B01J 23/26* | (2006.01) |
| *B01J 23/86* | (2006.01) |
| *B01J 27/10* | (2006.01) |
| *B01J 27/125* | (2006.01) |
| *B01J 27/128* | (2006.01) |
| *B01J 27/138* | (2006.01) |

(52) U.S. Cl.
CPC ............ *C07C 17/206* (2013.01); *B01J 21/18* (2013.01); *B01J 23/26* (2013.01); *B01J 23/866* (2013.01); *B01J 27/10* (2013.01); *B01J 27/125* (2013.01); *B01J 27/128* (2013.01); *B01J 27/138* (2013.01)

(58) Field of Classification Search
CPC ....... C07C 17/206; C07C 25/13; C07C 17/12; B01J 23/26; B01J 23/866; B01J 27/128; B01J 27/138

See application file for complete search history.

(56) References Cited

U.S. PATENT DOCUMENTS

| | | | |
|---|---|---|---|
| 2,745,886 A | 5/1956 | Ruh et al. | |
| 5,227,350 A | 7/1993 | Scott et al. | |
| 5,449,656 A | 9/1995 | Scott et al. | |
| 2010/0016607 A1* | 1/2010 | Dolbier, Jr. ............ | B01J 27/122 546/345 |

FOREIGN PATENT DOCUMENTS

| | | | | |
|---|---|---|---|---|
| EP | 0773061 | | 5/1997 | |
| GB | 2275924 A | * | 9/1994 | ........... C07C 17/206 |
| WO | WO2012098421 | | 7/2012 | |

OTHER PUBLICATIONS

Ventre et al., "Decarboxylative Fluorination of Aliphatic Carboxylic Acids via Photoredox Catalysis", Apr. 16, 2015, ACS Publications.

* cited by examiner

*Primary Examiner* — Jafar F Parsa

(57) ABSTRACT

The invention relates to process for the manufacture or preparation of fluorinated benzene, in particular monofluorobenzene, in a vapor-phase fluorination process. The process of the invention, for example, can comprise a batch or continuous manufacture or preparation of fluorinated benzene, in particular monofluorobenzene, using hydrogen fluoride (HF) in gas phase as fluorination gas. Also, in this process of the invention, for example, fluorination catalysts are involved.

12 Claims, No Drawings

PROCESS FOR PREPARING FLUOROBENZENE AND CATALYST THEREFORE

BACKGROUND OF THE INVENTION

Field of the Disclosure

The invention relates to process for the manufacture or preparation of fluorinated benzene, in particular monofluorobenzene, in a vapor-phase fluorination process. The process of the invention, for example, can comprise a batch or continuous manufacture or preparation of fluorinated benzene, in particular monofluorobenzene, using hydrogen fluoride (HF) in gas phase as fluorination gas. Also, in this process of the invention, for example, fluorination catalysts are involved.

Description of Related Art

Fluorobenzene is still prepared by Balz-Schiemann, Sandmeyer or Halex Reaction. All this types of reactions deliver good yields but are not environmental friendly at all. Especially in Asia plants are closed by authorities due to environmental problems which cannot be solved by this type of chemistries. It is known that carboxylic acids can be fluorinated and photolytic decarboxylated like in *J. Am. Chem. Soc.* 2015137175654-5657 (https://doi.org/10.1021/jacs.5b02244). But the described F-source (e.g. Selectfluor) is extremely expensive and NOT commercially available in large industrial volumes needed for fluorobenzene. A huge drawback is the huge skeleton of Selectfluor carrying the F-atom, and this skeleton cannot be recycled and so far needs to be incinerated. It is obvious that this described method is new but not feasible in industrial scale and regarding environmental aspects, even worse than Balz-Schiemann and Sandmeyer reactions.

Fluorinated organic compounds in industrial scale are prepared by fluorine halogen exchange using anhydrous HF, addition of HF to olefinic double bonds, fluorinating agents like amine×nHF, electrofluorination with HF (in situ generation of $F_2$) where in latter case selectivity, scalability and missing environmental friendliness (formation of very toxic partial fluorinated compounds) often is and remains an unsolved problem. Another existing fluorination procedure is using $F_2$-gas directly. But this requires—besides availability of industrial quantities—the very skilled handling of $F_2$-gas and co-produced HF (hydrogen (H) vs. fluorine (F) exchange reaction).

Fluorobenzene, as mentioned above, is still produced by Balz-Schiemann, Sandmeyer or Halex reactions. All of these reactions produce organic waste (toxic side products) and waste water often containing non-recyclable inorganic salts. Thus, these processes or the prior art are not environmentally friendly at all.

In the prior art some fluorination reactions in the gas phase using hydrogen fluoride and catalysts are described for aliphatic compounds, but not for aromatic systems like the benzene core.

Examples of such prior art processes can be found in the patent publications U.S. Pat. No. 2,745,886 (applied in 1955, to Dow Chemical), U.S. Pat. No. 5,227,350 (applied in 1992) and U.S. Pat. No. 5,449,656 (applied in 1995), both to ICI, in EP 0773061 (applied in 1994, to Atochem) and EP2665692 (applied in 2011, to Arkema).

The patent publication U.S. Pat. No. 2,745,886 (1955) relates to an improved fluorination catalyst, and to a process for fluorinating halohydrocarbons to highly fluorinated products with the aid of this catalyst. The U.S. Pat. No. 2,745,886 (1955) made the discovery that hydrated chromium fluoride may be activated with oxygen as therein particularly described, and that the material so activated is very effective in catalyzing the vapor-phase fluorination reaction of haloalkanes and hydrogen fluoride. In fact, the catalysts therein are believed to be basic chromium fluorides, are more active than $CrF_3$, or any of the catalysts known in the literature. They are also more effective in directing the course of the vapor-phase fluorination to greater conversions and yields of more highly fluorinated products, and at much lower temperatures, than has been achieved before.

The patent publication U.S. Pat. No. 5,227,350 (1992) relates to a method for regenerating a used fluorination catalyst such as a chromium-containing compound comprises contacting the used catalyst at a temperature of 300 DEG C. to 500 DEG C. with a mixture of an oxidizing agent, especially air, and hydrogen fluoride and optionally an inert diluent such as nitrogen, said mixture containing up to 30% of oxidizing agent on a molar basis. The method obviates chromium loss during regeneration/refluorination of spent catalyst and provides heated hydrogen fluoride for use directly in fluorination reactions.

The patent publication U.S. Pat. No. 5,449,656 (1995) relates to a chromium-containing fluorination catalyst which comprises an activity-promoting amount of zinc or a compound of zinc, a process for increasing the activity of a chromium-containing fluorination catalyst by introducing an activity promoting amount of zinc or a compound of zinc to the catalyst and a process for the production of fluorinated hydrocarbons, in particular 1,1,1,2-tetrafluoroethane which comprises reacting a hydrocarbon or a halogenated hydrocarbon, in particular 1-chloro-2,2,2-trifluoroethane with hydrogen fluoride in the vapor phase in the presence of the zinc-promoted chromium-containing catalyst The patent publication EP0773061 (1994) relates to chromium oxide or chromium oxides based catalysts and possibly one other catalytically active metal, of surface area greater than 100 $m^2/g$ are claimed. Manufacture of the catalyst is also claimed and consists of: a) forming an aqueous gelatinous precipitate of chromium hydroxide or chromium hydroxides and at least one other active metal; b) substituting water of the precipitate by a supercritical fluid gas in a continuous mode to form a porous solid and; c) calcining the resulting porous solid. Also claimed is the fluorination of halogeno saturated or unsaturated hydrocarbons chosen from fluoro compounds in C1-C5, in the gas phase by HF, using the above catalyst.

The patent publication EP 2665692 (2011)/WO2012098421 (A1) relates to a fluorination process, comprising:—an activation stage comprising contacting a fluorination catalyst with an oxidizing agent-containing gas flow for at least one hour; and—at least one reaction stage comprising reacting a chlorinated compound with hydrogen fluoride in gas phase in the presence of the fluorination catalyst, so as to produce a fluorinated compound.

However, today there is also a high demand of enabling large-scale and/or industrial production of fluorinated benzene involving a step of fluorination in a controlled and effective manner in a large-scale and/or industrial setting.

It is an object of the present invention to provide a high efficient process for the manufacture or for preparation of a fluorinated benzene, in particular monofluorobenzene, involving a step of fluorination, wherein in the fluorination process a fluorine gas (fluorination gas) comprising or consisting hydrogen fluoride (HF), which is largely available in large-scale, e.g., in industrial scale quantities, to be used for chemical synthesis, especially for the manufacture or for preparation of fluorobenzene compounds, in particular fluorobenzene (monofluorobenzene), as final products and/ or intermediates, for usage in agro-, pharma-, electronics-, catalyst, solvent and other functional chemical applications.

It is preferably another object of the present invention to provide a fluorination process for the manufacture or preparation of fluorinated benzene, in particular monofluorobenzene, involving a step of gas phase fluorination, e.g., fluorinating a benzene, using hydrogen fluoride gas (HF-gas), in order to enhance conversion and selectivity of chlorine-fluorine exchange reaction.

It is preferably still another object of the present invention to provide a fluorination process for the manufacture or preparation of a fluorinated benzene, in particular monofluorobenzene, involving a step of gas phase fluorination, e.g., fluorinating a benzene, using hydrogen fluoride gas (HF-gas), wherein the process can be performed in a large-scale (e.g., in kg-scale) and/or industrial production of fluorinated benzene.

SUMMARY OF THE INVENTION

The objects of the invention are solved as defined in the claims, and described herein after in detail.

The gas phase (vapor-phase) fluorination process of the present invention is using gaseous hydrogen fluoride (HF) as the fluorination gas. Most preferably, the gaseous hydrogen fluoride (HF) as the fluorination gas is "100%" gaseous hydrogen fluoride (HF), meaning that the gaseous hydrogen fluoride (HF) used is essentially consisting of anhydrous gaseous hydrogen fluoride (anhydrous HF). The term "anhydrous" has the commonly applied technical meaning in the technical field of chemistry. Accordingly, a substance is "anhydrous" if it contains no water. Many processes in chemistry can be impeded by the presence of water, therefore, it is important that water-free reagents and techniques are used. In practice, however, it is very difficult to achieve absolute dryness; anhydrous compounds gradually absorb water from the atmosphere so they must be stored and handled carefully to avoid such (re-)absorption of water. Techniques commonly known in the technical field of chemistry may be applied to prepare and to sustain gases, including gases of technical degree, essentially anhydrous.

Herein, the term "halogenated", "halogen" or the like terms, denotes a halogen atom other that fluorine (F), and particularly is meant to denote "chlorinated", or "chlorine" (Cl) or the like terms.

The numerical ranges disclosed herein include all values from, and including, the lower and upper value. For ranges containing explicit values (e.g., 1 to 7), any subrange between any two explicit values is included (e.g., 1 to 2; 2 to 6; 5 to 7; 3 to 7; 5 to 6; etc.).

The terms "comprising," "including," "having," and their derivatives, are not intended to exclude the presence of any additional component, step or procedure, whether or not the same is specifically disclosed. In order to avoid any doubt, all compositions claimed through use of the term "comprising" may include any additional additive, adjuvant, or compound, whether polymeric or otherwise, unless stated to the contrary. In contrast, the term, "consisting essentially of" excludes from the scope of any succeeding recitation any other component, step, or procedure, excepting those that are not essential to operability. The term "consisting of" excludes any component, step, or procedure not specifically delineated or listed. The term "or," unless stated otherwise, refers to the listed members individually as well as in any combination. Use of the singular includes use of the plural and vice versa.

Any pressure value or range of pressure values given herein in, i.e., "bar", unless otherwise stated refer to "bar absolute".

In this invention it now was found, in a particularly preferred embodiment, that especially fluorobenzenes can be prepared in gas phase (vapor-phase) in batch or preferred in continuous manner out of halogenated benzenes, e.g., monochlorobenzene, as precursors for producing fluorinated benzenes, e.g., monofluorobenzene. The principle of gas phase (vapor-phase) fluorination and especially with chromium (Cr) based catalysts applied for chlorine-fluorine exchange reaction of halogenated aliphatic compounds were disclosed already by Dow in 1955 in U.S. Pat. No. 2,745,886 (applied for in 1955).

The initial and/or preferred fluorination catalyst group of Cr-based catalysts used in the gas phase (vapor-phase) fluorination of the present invention, and used for preparing modifications of these Cr-based catalysts also used in the gas phase (vapor-phase) fluorination of the present invention, were prepared according to the recipe disclosed by Dow in 1955 in said U.S. Pat. No. 2,745,886. Therefore, disclosure of said U.S. Pat. No. 2,745,886 is incorporated herein for the purpose of chlorine-fluorine exchange reaction of halogenated aromatic compounds, such like in particular halogenated benzene compounds, in its entirety.

Surprisingly it was found by the present invention that the conditions described in U.S. Pat. No. 2,745,886 can be analogously applied to halogenated benzene compounds, despite their different reactivity as compared to the halogenated aliphatic compounds of U.S. Pat. No. 2,745,886. The active fluorinating species according to U.S. Pat. No. 2,745,886 is given to be $CrF_3$.

The fluorination catalyst may be employed, for example in pelletized form, as granules, or in form of a fluorination catalyst supported on a carrier, e.g., inorganic carrier, resistant to hydrogen fluoride (HF). Catalyst carrier may be also in form of pellets or granules, or may be any other support structure suitable to carry a gas phase (vapor-phase) catalyst, resistant to hydrogen fluoride (HF).

The gas phase (vapor-phase) fluorination process of the present invention can be performed as a batch process or as a continuous process. The skilled person will readily understand that additional equipment has to be used, as applicable in a batch process or in a continuous process, respectively, e.g., inlets, outlets, pipes, measurement equipment for pressure, temperature, flow-measurement and the like, are employed as commonly known in the field of art, even if not specifically indicated herein below for reason of conciseness only.

In the process of the present invention particular focus was put on a continuous gas phase (vapor-phase) fluorination process of halogenated benzenes, e.g., of chlorinated benzene, to produce fluorinated benzenes, e.g., monofluorobenzene, as the gas phase (vapor-phase) fluorination product. Accordingly, also in case of a continuous gas phase (vapor-phase) fluorination step according to the present invention, the skilled person will readily understand that additional equipment has to be used for such continuous gas phase (vapor-phase) fluorination, e.g., inlets, outlets, pipes, measurement equipment for pressure, temperature, flow-measurement and the like, as applicable, are employed as commonly known in the field of art, even if not specifically indicated herein below for reason of conciseness only.

An exemplary apparatus for preparing, activating and/or re-activating the fluorination catalyst employed in the present invention, and/or for the gas phase (vapor-phase) fluorination process of the present invention, for example, is a reactor consisting out of a Monel-tube filled with catalyst pellets, a HF feeding system out of a stainless steel cylinder pressurized with $N_2$ (dosage from liquid phase over a Bronkhorst flow meter), a vaporizer operated at 180° C. for the halogenated benzene feed, e.g., monochlorobenzene (chlorobenzene) feed, a condenser with a reservoir after the tube reactor still under slight overpressure, a scrubber just filled with water kept (cooled) at 25° C. and another scrubber filled with NaOH and a bubble counter at the exit allowing exhaust gas and the $N_2$ to exit.

For the gas phase (vapor-phase) fluorination process of the present invention, for example, the Monel tube (d=10 cm, volume around 6.5 l, electrically heated) is filled with a kg-scale quantity of the fluorination catalyst, for example at least 1 kg of the fluorination catalyst, preferably at least 2 kg, 3 kg, or 4 kg, more preferably at least 5 kg, or even at least 6 kg, 7 kg, 8 kg or 9 kg of the fluorination catalyst. The Monel tube is (electrically) heated to the reaction temperature of at least about 200° C., preferably of at least about 250° C., more preferably to a reaction temperature of about 280° C., and then the feed into the monel tube, of HF feed and halogenated benzene feed, e.g., monochlorobenzene (chlorobenzene) feed, was adjusted in relation to the employed kg-scale quantity of the fluorination catalyst, for example, based on 1 kg of the fluorination catalyst, the feed is adjusted to about 0.667 kg/h (3.33 mol/h) HF and about 1.11 mol/h halogenated benzene (about 0.125 kg/h based on chlorobenzene), both feeds fed over the vaporizer, which is operated at 180° C. for 1 h. Carefully hydrolyzed samples (see below), taken during the described gas phase (vapor-phase) fluorination process of the present invention from the fluorination product reservoir, showed almost quantitative conversion of halogenated benzene. The reaction time can be adjusted in relation to the employed quantity of fluorination catalyst on the one hand, and the quantity of HF feed and or halogenated benzene feed, e.g., monochlorobenzene (chlorobenzene) feed on the other hand.

In an example, the feed into the monel tube, of HF feed and chlorobenzene feed, was adjusted in relation to the employed 9 kg-scale quantity of the fluorination catalyst, to 0.60 kg/h (30.0 mol/h) HF and 1.126 kg/h (10.0 mol/h) chlorobenzene, both feeds fed over the vaporizer, which is operated at 180° C. for 1 h. A carefully hydrolyzed sample (see below), taken during the described gas phase (vapor-phase) fluorination process of the present invention from the fluorination product reservoir, showed almost quantitative conversion of chlorobenzene.

It goes without saying that it is apparent to the person skilled in the art to also use any other reactor equipment suitable for catalytic gas phase reactions, fitted to be resistant to hydrogen fluoride (HF).

According to the vapor-phase fluorination process of the invention a reaction temperature is to be achieved and sustained at a vapor-phase reaction temperature in a range of from about 200° C. to about 300° C., preferably in a range of from about 250° C. to about 300° C., more preferably in a range of from about 270° C. to about 290° C.; and for example of about 280° C.

All materials, e.g., gas phase (vapor-phase) fluorination product (e.g., fluorinated benzenes, preferably monofluorobenzene), obtained in the gas phase (vapor-phase) fluorinations of the present invention leaving the reactors were collected by means of a condenser with a (product) reservoir.

After having finished the gas phase (vapor-phase) fluorination, the collected gas phase (vapor-phase) fluorination product is worked up, by hydrolysis, by pouring the collected gas phase (vapor-phase) fluorination product very carefully into cooled water, preferably cooled water at a temperature of about 0° C. to about 10° C., more preferably cooled water at a temperature of about 0° C. to about 5° C. In a particular example, the gas phase (vapor-phase) fluorination product, obtained is carefully poured into ice water. The fluorinated product, e.g., the fluorinated benzenes, e.g., monofluorobenzene, is further worked up by phase separation of the organic phase from the water phase, comprising the fluorinated benzenes, e.g., monofluorobenzene, and optionally can be further purified by distillation of the organic phase at atmospheric pressure, to obtain the purified the fluorinated benzenes, e.g., purified monofluorobenzene.

The vapor-phase fluorination reaction of this invention is shown in Scheme 1.

Scheme 1: Vapor-phase fluorination over fluorination catalyst.

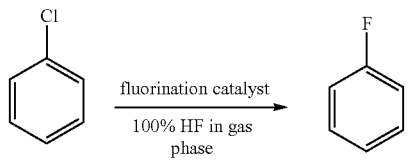

The gas phase (vapor-phase) fluorinations of the present invention are monitored for the activity and/or exhaustion of the fluorination catalyst, by analyzing hydrolyzed samples of gas phase (vapor-phase) fluorination product, taken from the vapor-phase fluorination product reservoir, for any non-converted starting material of halogenated benzenes, e.g., of chlorinated benzene. The hydrolysis of the said samples is performed as described above. If a content of at maximum about 5% of non-converted halogenated benzenes, e.g., of chlorinated benzene, is observed, relative to the total mixture of halogenated benzenes, e.g., of chlorinated benzene, as starting material, and of the produce fluorinated benzenes, e.g., monofluorobenzene, as the gas phase (vapor-phase) fluorination product, taken together as 100% (e.g., percentage on molar basis). The said percentage (%) of non-converted halogenated benzenes, e.g., of chlorinated benzene, can be determined by conventional methods, for example, gas chromatography, related to standardized samples of starting material and product materials, and mixtures thereof.

DESCRIPTION OF THE PREFERRED EMBODIMENTS

As briefly described in the Summary of the Invention, and defined in the claims and further detailed by the following description and examples herein.

In particular, the present invention relates to a process for the manufacture of a fluorinated benzene, preferably monofluorobenzene, in a vapor-phase fluorination process comprising the steps of:
  a) provision of a chlorinated benzene as starting compound;
  b) provision of a fluorination gas consisting of anhydrous hydrogen fluoride (HF);
  c) provision of a fluorination catalyst, optionally of an activated and/or reactivated, and/or of a pre-fluorinated fluorination catalyst;

d) provision of a reactor or reactor system, resistant to hydrogen fluoride (HF), and comprising a vaporizer for the starting compound of a), and a condenser for the vapor-phase fluorination reaction product, and a reservoir for collecting the fluorination reaction product;

e) at least one vapor-phase reaction stage comprising reacting of a) a vaporized chlorinated benzene with b) anhydrous hydrogen fluoride (HF) in gas phase in the presence of c) the fluorination catalyst, so as to produce a vapor-phase fluorination reaction product;

f) withdrawing the vapor-phase fluorination reaction product formed in the vapor-phase reaction step e) from the reactor or reactor system of d), and transferring the vapor-phase fluorination reaction product to the condenser and condensing for collecting the condensed fluorination reaction product; and g) hydrolysing the fluorination reaction product obtained and collected according to f), in water, to obtain a fluorinated benzene, preferably monofluorobenzene; and h) phase separation of the organic phase of fluorinated benzene, preferably monofluorobenzene, from water phase to obtain fluorinated benzene, preferably monofluorobenzene; and g) optionally purifying the fluorinated benzene, preferably monofluorobenzene, obtained in h) by distillation under atmospheric pressure to obtain purified fluorinated benzene, preferably purified monofluorobenzene.

The inventive process disclosed hereunder delivers fluorobenzene in high yield in environmental friendly and economic feasible manner involving a step of a gas-phase fluorination of a halogenated, preferably chlorinated, benzenze with HF-gas to obtain the corresponding a fluorinated benzene, preferably monofluorobenzene. The general gas-phase (vapor-phase) fluorination reaction step is given above in Scheme 1.

If the halogenated benzene employed in the present invention as a starting material contains more than one halogen, e.g., chlorine, the then multi-fluorinated benzenes, are obtained by the vapor-phase chlorine-fluorine exchange or fluorination reaction.

In particular, according to the present invention the halogenated benzene preferably is chlorobenzene (monochlorobenzene), and the fluorinated benzene then is preferably fluorobenzene (monofluorobenzene).

As a reference for scale orientation, and for reason of calculating quantities, reference is made to the molecular weight of benzene of 78.114 g/mol, and of monofluorobenzene of 96.10 g/mol.

For reason of adapting and/or controlling process parameters, here the boiling point of benzene of about 80° C., and that of monofluorobenzene of about 85° C. are also given, each for ambient pressure.

In an embodiment, the invention relates to a process for the manufacture of a fluorinated a fluorinated benzene, wherein the fluorination catalyst is selected from the group consisting of $Cr_2O_3$ based catalyst, $MGF_2$ based catalyst, $SbCl_5/C$ based catalyst, and $FeCl_3/C$ based catalyst.

In an embodiment, the invention relates to a process for the manufacture of a fluorinated benzene as described herein and in the claims, wherein the fluorination catalyst is selected from the group consisting of $MgF_2$ based catalyst, $SbCl_5/C$ based catalyst, and $FeCl_3/C$ based catalyst, and wherein the said catalyst is pre-fluorinated with hydrogen fluoride (HF).

In an embodiment, the invention relates to a process for the manufacture of a fluorinated benzene as described herein and in the claims, wherein the fluorination catalyst is selected from the group $Cr_2O_3$ based catalyst.

In an embodiment, the invention relates to a process for the manufacture of a fluorinated benzene as described herein and in the claims, wherein the $Cr_2O_3$ based catalyst is an activated and/or re-activated $Cr_2O_3$ based catalyst.

In an embodiment, the invention relates to a process for the manufacture of a fluorinated benzene as described herein and in the claims, wherein the activated and/or re-activated $Cr_2O_3$ based catalyst is activated and/or re-activated by treatment with an oxygen containing gas; and/or wherein the $Cr_2O_3$ based catalyst, preferably the activated and/or re-activated $Cr_2O_3$ based catalyst, is pre-fluorinated with hydrogen fluoride (HF).

In an embodiment, the invention relates to a process for the manufacture of a fluorinated benzene as described herein and in the claims, wherein the activated and/or re-activated $Cr_2O_3$ based catalyst is activated and/or re-activated by treatment with Zn dopant, preferably by treatment with $ZnCl_2$ as dopant, by treatment with Ni dopant, preferably by treatment with $NiCl_2$ as dopant.

In an embodiment, the invention relates to a process for the manufacture of a fluorinated benzene as described herein and in the claims, wherein the activated and/or re-activated $Cr_2O_3$ based catalyst is activated and/or re-activated by treatment with Ni dopant, preferably by treatment with $NiCl_2$ as dopant, and wherein the said Ni dopant activated and/or re-activated $Cr_2O_3$ based catalyst is supported on $AlF_3$ as a carrier.

In an embodiment, the invention relates to a process for the manufacture of a fluorinated benzene as described herein and in the claims, wherein the activated and/or re-activated $Cr_2O_3$ based catalyst is activated and/or re-activated by treatment with Mg dopant, preferably by treatment with Mg as dopant, and wherein the said Mg dopant activated and/or re-activated $Cr_2O_3$ based catalyst is additionally treated with carbon (C) to yield an activated and/or re-activated Cr—Mg—C fluorination catalyst.

In an embodiment, the invention relates to a process for the manufacture of a fluorinated benzene as described herein and in the claims, wherein in the said process for the manufacture of a fluorinated benzene in e) the at least one vapor-phase reaction stage is comprising reacting of a) a vaporized chlorinated benzene with b) anhydrous hydrogen fluoride (HF) in gas phase in the presence of c) the fluorination catalyst, so as to produce a vapor-phase fluorination reaction product, is performed in a reactor or reactor system of d) which is heated to the reaction temperature of at least about 200° C., preferably of at least about 250° C., more preferably to a reaction temperature of about 280° C.; and then the feed into the reactor or reactor system of d), of hydrogen fluoride (HF) feed and halogenated benzene feed, preferably monochlorobenzene (chlorobenzene) feed, is adjusted in relation to the employed kg-scale quantity of the fluorination catalyst of c), based on 1 kg of the fluorination catalyst, such that the said feed is adjusted to about 3.33 mol/h (0.667 kg/h) HF and about 1.11 mol/h halogenated benzene (about 0.125 kg/h based on chlorobenzene), both feeds fed over the vaporizer, which is operated at 180° C., and based on an operation period of the vaporizer of 1 h.

An advantageous a reactor or reactor system d), resistant to hydrogen fluoride (HF), is a Monel tube, preferably a Monel tube that is electrically heated. For example, the Monel tube can have the following exemplary dimension, of a diameter (d) of about 10 cm, and a volume of about 6.5 l.

Preferably the Monel tube is equipped with an electrical heater capable to achieve and sustain a vapor-phase reaction temperature in a range of from about 200° C. to about 300° C., preferably in a range of from about 250° C. to about 300° C., more preferably in a range of from about 270° C. to about 290° C.; and for example of about 280° C.

FURTHER DETAILS OF THE INVENTION

As briefly described in the Summary of the Invention, and defined in the claims and further detailed by the following description and examples herein, The process of the present invention, in case of using chromium (Cr) based fluorination catalysts, is further related to a vapor-phase fluorination process, comprising a fluorination catalyst activation stage comprising contacting the fluorination catalyst with an oxidizing agent-containing gas flow for at least one hour; before and/or during the at least one reaction stage comprising reacting a halogenated benzene, e.g., chlorinated benzene, as starting material with hydrogen fluoride (HF) in gas phase in the presence of the chromium (Cr) based fluorination catalyst, so as to produce a fluorinated benzene.

For example, the process of the present invention can comprise a plurality of reaction stages alternating with a plurality of regeneration stages, wherein the reaction stages comprises reacting the chlorinated compound with hydrogen fluoride in gas phase in the presence of the fluorination catalyst, and the regeneration stages comprise contacting the fluorination catalyst with an oxidizing agent-containing gas flow.

For example, the process of the present invention can be performed such that the oxidizing agent-containing gas flow of the activation stage and/or the regeneration stages is an oxygen-containing gas flow.

For example, the process of the present invention can be performed such that the activation stage and/or the regeneration stages comprise contacting the fluorination catalyst with the oxidizing agent-containing gas flow for at least 2 hours, preferably for at least 4 hours, more preferably for at least 10 hours, and even more preferably for at least 15 hours.

For example, the process of the present invention can be performed such that the oxidizing agent-containing gas flow of the activation stage and/or the regeneration stages contains hydrogen fluoride in addition to the oxidizing agent, and wherein the proportion of oxidizing agent in the oxidizing agent-containing gas flow of the activation stage and/or the regeneration stages is preferably from 2 to 98 mol-%, and more preferably from 5 to 50 mol-%, relative to the total amount oxidizing agent and hydrogen fluoride.

For example, the process of the present invention can be performed such that the oxidizing agent-containing gas flow of the activation stage and/or the regeneration stages does not contain hydrogen fluoride, and preferably is air.

For example, the process of the present invention can be performed such that the activation stage and/or the regeneration stages comprise contacting the fluorination catalyst with a hydrogen fluoride gas flow, either before contacting the fluorination catalyst with the oxidizing agent-containing gas flow; or after contacting the fluorination catalyst with the oxidizing agent-containing gas flow.

For example, the process of the present invention can be performed such that the activation stage comprises a preliminary step of reacting the halogenated, e.g., the chlorinated, benzene as the starting material with hydrogen fluoride (HF) in gas phase in the presence of the fluorination catalyst, prior to contacting the halogenated, e.g., the chlorinated, benzene as the starting material with the oxidizing agent-containing gas flow.

For example, the process of the present invention can be performed such that the oxidizing agent-containing gas flow is contacted with the fluorination catalyst during the activation stage and/or the regeneration stages at a temperature of from 250 to 500° C., preferably from 300 to 450° C., more preferably from 350 to 450° C.

For example, the process of the present invention can be performed such that the fluorination catalyst is a supported catalyst, and is preferably supported on a support selected from fluorinated alumina, fluorinated chromia, fluorinated activated carbon or graphite carbon.

For example, the process of the present invention can just be performed such that the fluorination catalyst is an unsupported catalyst.

For example, the process of the present invention can be performed such that the fluorination catalyst further comprises a co-catalyst selected from Co, Zn, Mn, Mg, V, Mo, Te, Nb, Sb, Ta, P, Ni or mixtures thereof, preferably Ni, and wherein said co-catalyst is preferably present in an amount from about 1 wt.-% to about 10 wt.-% of said fluorination catalyst.

For example, the process of the present invention can be performed such that the fluorination catalyst is a mixed chromium/nickel catalyst, the atomic ratio of nickel to chromium being preferably from about 0.5 to about 2 and more preferably approximately 1.

For example, the process of the present invention can be further performed such that the molar ratio of hydrogen fluoride (HF) to halogenated, e.g., the chlorinated, benzene as the starting material is from about 2:1 to about 15:1, preferably about 3:1 to about 10:1, more preferably about 3:1 to about 5:1.

For example, the process of the present invention can be further performed such that the reaction stages are carried out at a pressure of from about 1 to about 20 bar, preferably from about 5 to about 15 bar, more preferably from about 7 to about 10 bar.

The Cr-Based Catalysts:

The general gas-phase (vapor-phase) fluorination reaction step with hydrogen fluoride (HF) as fluorination gas and fluorination catalyst based on chromium, for example, $Cr_2O_3$, is shown in representative Scheme 2.

Scheme 2: Gas phase fluorination with HF and catalyst (here, for example, $Cr_2O_3$)

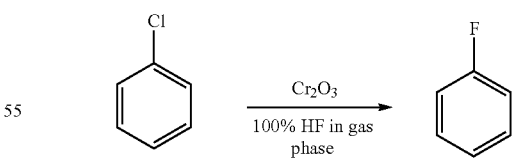

The patent publication U.S. Pat. No. 2,745,886 (1955), as already described above, relates to a fluorination catalyst, and to a process for fluorinating halohydrocarbons to highly fluorinated products with the aid of this catalyst.

In the present invention the fluorination catalyst of the U.S. Pat. No. 2,745,886 (1955) is analogously used for the gas-phase (vapor-phase) fluorination reaction step with hydrogen fluoride (HF) as fluorination gas. Herein the hydrated chromium fluoride may be activated with oxygen as particularly described in the U.S. Pat. No. 2,745,886 (1955), and that the catalyst material so activated is very effective in catalyzing the vapor-phase fluorination reaction of halogenated, e.g., the chlorinated, benzene as the starting material and hydrogen fluoride (HF) as the fluorination gas. In fact, the catalysts are believed to be basic chromium fluorides, and more active than $CrF_3$. The said catalysts are also more effective in directing the course of the vapor-phase fluorination to greater conversions and yields of more highly fluorinated products, and at much lower temperatures, than has been achieved before.

In a particular embodiment of the present invention, the fluorination catalyst was prepared according to example 3 part B as described U.S. Pat. No. 2,745,886 starting with $Cr_2O_3$ (99% purity) and HF (anhydrous, 100%) giving $CrF_3 \times 3H_2O$, and, after adding 2 wt.-% graphite and formation of pellets, the catalyst was activated with oxygen.

In analogy to example 3 part B as described U.S. Pat. No. 2,745,886, the catalyst in accordance with the present invention was prepared by passing a stream of oxygen through a bed of 3/16 inch by 3/16 inch disc-shaped pellets containing 2 weight percent graphite prepared according to the following procedure:

A catalyst in accordance with the invention was prepared by reacting high purity chromium trioxide ($CrO_3$) with an excess of 70 weight percent hydrofluoric acid. The semi-crystalline bright green reaction product was heated in a drying oven at 80° C. to sensible dryness. This sensibly dry product, consisting preponderantly of α-$CrF_3 \times 3H_2O$ was ground to pass through a 10 mesh screen, admixed with 2 weight percent graphite, and was pressed into 3/16 inch by 3/16 inch disc-shaped pellets.

The dimensions of the catalyst bed and the conditions of the activation step were the same as described in example 3 of U.S. Pat. No. 2,745,886, except that oxygen was employed instead of air, e.g., according to the following procedure:

The catalyst pellets produced as described here-above were packed to a height of about 12 inches in the 2 inch nickel reaction tube as described in the examples of U.S. Pat. No. 2,745,886, or alternatively or preferably, into a Monel tube as described herein-above and employed in in the context of the present invention. The catalyst pellets were then activated by heating them to, and holding them for two hours at, 500° C. in a stream of oxygen. Of course, alternatively also air as described in example of U.S. Pat. No. 2,745,886 can be used.

The Cr-based catalysts prepared above are amorphous to X-ray diffraction analysis.

For example, the process of preparing a Cr-based fluorination catalysts for use in the vapor-phase process of the present invention can be performed such that the method of preparing a catalyst useful in promoting the fluorination by vapor-phase reaction with hydrogen fluoride, said method comprising heating a mixture of a major proportion of hydrated chromium fluoride and a minor proportion of chromium trioxide at a temperature above about 400° C. for a time sufficiently long to convert at least part of the hydrated chromium fluoride to a basic chromium fluoride.

For example, the process of preparing a Cr-based fluorination catalysts for use in the vapor-phase process of the present invention can be performed such that the method of preparing a catalyst useful in promoting the fluorination by vapor-phase reaction with hydrogen fluoride, said method consisting essentially of heating a hydrated chromium fluoride to a temperature in the range of from about 350° to 750° C. in the presence of oxygen.

For example, the process of preparing a Cr-based fluorination catalysts for use in the vapor-phase process of the present invention can be performed such that the method of preparing a catalyst useful in promoting the fluorination by vapor-phase reaction with hydrogen fluoride, said method consisting essentially of heating a hydrated chromium fluoride to. a temperature in the range of from about 350° C. to about 650° C., while passing a: stream of a gas comprising molecular oxygen therethrough for a time sufficiently long for a small though effective amount of oxygen to react therewith.

For example, the process of preparing a Cr-based fluorination catalysts for use in the vapor-phase process of the present invention can be performed such that in the said process the gas stream is oxygen.

For example, the process of preparing a Cr-based fluorination catalysts for use in the vapor-phase process of the present invention can be performed such that in the said process the gas stream is air.

For example, the process of preparing a Cr-based fluorination catalysts for use in the vapor-phase process of the present invention can be performed such that the said method is comprising heating a bed of $CrF_3 \times 3H_2O$ to an activation temperature in the range of from 350° to 650° C., while passing a stream of a gas comprising molecular oxygen therethrough, the flow of gas being maintained through said bed within said activation temperature range for a time sufficiently long to convert at least part of the hydrated chromium fluoride to a basic chromium fluoride.

For example, the process of preparing a Cr-based fluorination catalysts for use in the vapor-phase process of the present invention can be performed such that the said the $CrF_3 \times 3H_2O$ is the alpha hydrate.

In the context of the present invention the material "Hastelloy®" is mentioned, and therefore shall be explained in more detail hereinafter.

Hastelloy® C is an alloy represented by the formula NiCr21Mo14W, alternatively also known as "alloy 22" or "Hastelloy® C-22. The said alloy is well known as a corrosion resistant nickel-chromium-molybdenum-tungsten alloy and has excellent resistance to oxidizing reducing and mixed acids. The said alloy is used in flue gas desulphurization plants, in the chemical industry, environmental protection systems, waste incineration plants, sewage plants. Apart from the before said example, in other embodiments of the invention, in general nickel-chromium-molybdenum-tungsten alloy from other manufactures, and as known to the skilled person, of course can be employed in the present invention. A typical chemical composition (all in weight-%) of such nickel-chromium-molybdenum-tungsten alloy is, each percentage based on the total alloy composition as 100%: Ni (nickel) as the main component (balance) of at least about 51.0%, e.g. in a range of from about 51.0% to about 63.0%; Cr (chromium) in a range of from about 20.0 to about 22.5%, Mo (molybdenum) in a range of from about 12.5 to about 14.5%, W (tungsten or wolfram, respectively) in a range of from about 2.5 to about 3.5%; and Fe (iron) in an amount of up to about 6.0%, e.g. in a range of from about 1.0% to about 6.0%, preferably in a range of from about 1.5% to about 6.0%, more preferably in a range of from about 2.0% to about 6.0%.

Optionally, the percentage based on the total alloy composition as 100%, Co (cobalt) can be present in the alloy in an amount of up to about 2.5%, e.g. in a range of from about 0.1% to about 2.5%. Optionally, the percentage based on the total alloy composition as 100%, V (vanadium) can be present in the alloy in an amount of up to about 0.35%, e.g. in a range of from about 0.1% to about 0.35%. Also, the percentage based on the total alloy composition as 100%, optionally low amounts (i.e. ≤0.1%) of other element traces, e.g. independently of C (carbon), Si (silicon), Mn (manganese), P (phosphor), and/or S (sulfur). In such case of low amounts (i.e. ≤0.1%) of other elements, the said elements e.g. of C (carbon), Si (silicon), Mn (manganese), P (phosphor), and/or S (sulfur), the percentage based on the total alloy composition as 100%, each independently can be present in an amount of up to about 0.1%, e.g. each independently in a range of from about 0.01 to about 0.1%, preferably each independently in an amount of up to about 0.08%, e.g. each independently in a range of from about 0.01 to about 0.08%. For example, said elements e.g. of C (carbon), Si (silicon), Mn (manganese), P (phosphor), and/or S (sulfur), the percentage based on the total alloy composition as 100%, each independently can be present in an amount of, each value as an about value: C≤0.01%, Si≤0.08%, Mn≤0.05%, P≤0.015%, S≤0.02%. Normally, no traceable amounts of any of the following elements are found in the alloy compositions indicated above: Nb (niobium), Ti (titanium), Al (aluminum), Cu (copper), N (nitrogen), and Ce (cerium).

Hastelloy® C-276 alloy was the first wrought, nickel-chromium-molybdenum material to alleviate concerns over welding (by virtue of extremely low carbon and silicon contents). As such, it was widely accepted in the chemical process and associated industries, and now has a 50-year-old track record of proven performance in a vast number of corrosive chemicals. Like other nickel alloys, it is ductile, easy to form and weld, and possesses exceptional resistance to stress corrosion cracking in chloride-bearing solutions (a form of degradation to which the austenitic stainless steels are prone). With its high chromium and molybdenum contents, it is able to withstand both oxidizing and non-oxidizing acids, and exhibits outstanding resistance to pitting and crevice attack in the presence of chlorides and other halides. The nominal composition in weight-% is, based on the total composition as 100%: Ni (nickel) 57% (balance); Co (cobalt) 2.5% (max.); Cr (chromium) 16%; Mo (molybdenum) 16%; Fe (iron) 5%; W (tungsten or wolfram, respectively) 4%; further components in lower amounts can be Mn (manganese) up to 1% (max.); V (vanadium) up to 0.35% (max.); Si (silicon) up to 0.08% (max.); C (carbon) 0.01 (max.); Cu (copper) up to 0.5% (max.).

The following examples are intended to further illustrate the invention without limiting its scope.

EXAMPLES

Representative, example procedures are described hereinafter in the embodiment following examples. In the process of the present invention particular focus was put on a continuous gas phase (vapor-phase) fluorination step. Accordingly, the skilled person will readily understand that additional equipment has to be used, as applicable, e.g., inlets, outlets, pipes, measurement equipment for pressure, temperature, flow-measurement and the like, are employed as commonly known in the field of art, even if not specifically indicated herein below for reason of conciseness only.

Example 1

Synthesis of Fluorobenzene in Gas Phase Over $Cr_2O_3$ Based Catalyst.

The fluorination catalyst was prepared according to example 3 part B in U.S. Pat. No. 2,745,886 starting with $Cr_2O_3$ (99% purity) and HF (anhydrous, 100%) giving $CrF_3 \times 3\,H_2O$ and—after adding 2 wt % graphite and formation of pellets, the catalyst was activated with oxygen. See description below.

Scheme 2: Vapor-phase fluorination with $Cr_2O_3$ based catalyst.

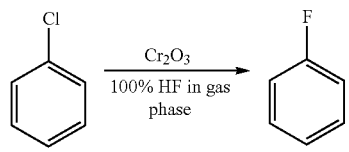

Preparation of Vapor-Phase Fluorination Catalyst:

In analogy to example 3 part B as described U.S. Pat. No. 2,745,886, the catalyst in accordance with the present invention was prepared by passing a stream of oxygen through a bed of 3/16 inch by 3/16 inch disc-shaped pellets containing 2 weight percent graphite prepared according to the following procedure:

A catalyst in accordance with the invention was prepared by reacting high purity chromium trioxide ($CrO_3$) with an excess of 70 weight percent hydrofluoric acid. The semi-crystalline bright green reaction product was heated in a drying oven at 80° C. to sensible dryness. This sensibly dry product, consisting preponderantly of α-$CrF_3 \times 3H_2O$ was ground to pass through a 10 mesh screen, admixed with 2 weight percent graphite, and was pressed into 3/16 inch by 3/16 inch disc-shaped pellets.

The dimensions of the catalyst bed and the conditions of the activation step were the same as described in example 3 of U.S. Pat. No. 2,745,886, except that oxygen was employed instead of air, e.g., according to the following procedure:

The catalyst pellets produced as described here-above were packed to a height of about 12 inches in the 2 inch nickel reaction tube as described in the examples of U.S. Pat. No. 2,745,886, or alternatively or preferably, into a Monel tube as described herein-above and employed in in the context of the present invention. The catalyst pellets were then activated by heating them to, and holding them for two hours at, 500° C. in a stream of oxygen. Of course, alternatively also air as described in example of U.S. Pat. No. 2,745,886 can be used.

The catalysts prepared above are amorphous to X-ray diffraction analysis.

Apparatus for Vapor-Phase Fluorination:

The reactor consists out of a Monel-tube filled with catalyst pellets, a HF feeding system out of a stainless steel cylinder pressurized with $N_2$ (dosage from liquid phase over a Bronkhorst flow meter), a vaporizer operated at 180° C. for the chlorobenzene feed, a condenser with a reservoir after the tube reactor still under slight overpressure, a scrubber just filled with water kept (cooled) at 25° C. and another scrubber filled with NaOH and a bubble counter at the exit allowing exhaust gas and the $N_2$ to exit.

Vapor-Phase Fluorination Process:

The Monel tube (d=10 cm, volume around 6.5 l, electrically heated) was filled with 9 kg catalyst. Once the reactor temperature reached 280° C., the feed was adjusted to 600 g/h (30.0 mol/h) HF and 1126 g/h (10.0 mol/h) chlorobenzene, both fed over the vaporizer, which is operated at 180° C. for 1 h, into the monel tube. A carefully hydrolyzed sample during the reaction showed almost quantitative conversion of chlorobenzene.

Collection of Vapor-Phase Fluorination Product:

All material collected in the reservoir of the condenser was very carefully fed into ice water and the organic phase carefully distilled at atmospheric pressure in a distillation apparatus out of plastics to get 99.9% pure fluorobenzene at 85° C. transition temperature. The isolated yield was 723 g fluorobenzene (75% of theory).

Example 2

Lifetime Experiment

Trial 1 was repeated in a fully automated apparatus (in a 100 h pilot scale run). Samples taken every 5 h showed a continuous degradation (deactivation) of the catalyst (conversion rate analyze by GC). After 55 h, the conversion of chlorobenzene dropped to 56% only, after 100 h only a 10% conversion was observed and the experiment was stopped (a 100 l/h $N_2$-stream was continued for about 2 h to get out HF and organic volatile material).

Example 3

Reactivation of $Cr_2O_3$ Catalyst.

The principle of reactivation of lower performance Cr-based fluorination catalysts is known from U.S. Pat. No. 5,227,350 (1992).

The reactor was heated to 350° C. ($N_2$-stream still open) and a synthetic air flow was started with an oxygen concentration at the beginning of 0.5% $O_2$ and 95% $N_2$, increased to an $O_2$ concentration of 1% after 1 h. An exothermicity could be observed. Over 5 h, the $O_2$ concentration was increased by 1% every hour to reach 5% after 5 h. It could be observed that a hot spot area moved from the entrance to the exit of the reactor over this time period. The $O_2$ was stopped but the $N_2$-purge was continued at 400° C. reactor temperature for another 5 h to remove (formed) moisture and oxygen absorbed on the catalyst. Afterwards the $Cr_2O_3$ was pretreated with HF at 200° C. reactor temperature for 1 h with a HF feed of 100 g/h for 15 min continued with an HF feed of 200 g/h for the remaining 45 minutes.

Example 4

Fluorination of Chlorobenzene with Reactivated $Cr_2O_3$-Catalyst

This trial was done according to example 1. If any, only a very slight deactivation vs. example 1 was observed by showing 5% chlorobenzene in a hydrolyzed sample of the reservoir of the condenser. The obtained yield in fluorobenzene based on converted chlorobenzene again was 75% of theory.

Example 5

Fluorination of Chlorobenzene with $MgF_2$ Catalyst.

A $MgF_2$ based catalyst containing 10% CsCl and 90% $MgF_2$ was prepared and filled as pellets into the reactor tube, the catalyst was pre-fluorinated 1 h with HF and the trial was performed according to example 1. The conversion into chlorobenzene was 60%, the selectivity to fluorobenzene 87%.

Example 6

Fluorination of Chlorobenzene with $SbCl_5$/C-Catalyst.

A 50% $SbCl_5$ based catalyst on active carbon (Norrit RB3) was prepared and filled as pellets into the reactor tube, the catalyst was treated with Cl2-gas (100 g/h) for 0.5 h at 60° C. to be sure to have 100% active $SbCl_5$ and not $SbC_3$) and afterwards also pre-fluorinated 1 h with HF; the procedure was performed according to example 1. The conversion in chlorobenzene was 96%, the selectivity to fluorobenzene 98%.

Example 7

Fluorination of Chlorobenzene with $FeCl_3$/C-Catalyst.

A 90% $FeCl_3$ based catalyst on active carbon (Norrit RB3) was prepared and filled as pellets into the reactor tube, the catalyst was pre-fluorinated 1 h with HF, the trial was performed according to example 1. The conversion in chlorobenzene was 73%, the selectivity to fluorobenzene 92%.

Example 8

Fluorination of Chlorobenzene with Zn Activated Cr-Catalyst.

The catalyst was prepared according to the principle disclosed first time in ICI's U.S. Pat. No. 5,449,656 from 1955 example 3, the Zn content was adjusted to 3%.

1 kg (19.2 mol) of chromia in form of granules of size 0.5-1.4 mm and surface of 50 $m^2$/g (Strem chemicals) was added to a solution of 78.6 g (0.5769 mol) $ZnCl_2$ in 1 l distilled water and stirred for 1 h at room temperature. Afterwards, the material was dried in vacuum (20 mbar/60° C.) until no weight loss could be observed resulting in particles of size 0.5-1.4 mm with 3 wt % Zn. A Monel tube of 10 cm diameter and 40 cm length was filled with the catalyst and HF (100%) was added over a Bronkhorst flow meter for 1 h in a flow rate of 500 g/h and a temperature of 250° C. After 1 h pre-treatment with HF only, 0.5 wt % oxygen was mixed into the HF feed for another 3 hour. Chlorobenzene feed was started over a vaporizer (operated at 180° C.) with a feed of 100 g/h (0.88 mol) and a HF feed of 352.2 g (17.6 mol) at a temperature of 230° C. Operating time was 2 h. The analytical results are similar to the no Zn containing catalyst (out of example 1).

The conversion of chlorobenzene was quantitative, the selectivity to fluorobenzene 99% giving 160 g fluorobenzene (95% of theory) isolated after careful work up into ice water, phase separation and distillation at atmospheric pressure.

Example 9

Fluorination of Chlorobenzene with Ni-Doped Cr-Catalysts.

Elf Atochem in EP0773061 (1994) describes the usage of Ni doped Cr-catalysts prepared out of $Cr(NO_3)_3$ and $NiCl_2$. The catalyst was prepared according to example 1 in the Elf Atochem patent. The inventive procedure described in example 1 in this patent but at 260° C. gave 94% conversion and a selectivity to fluorobenzene of 98%. The achieved purity after hydrolysis and distillation was 99.9%, the isolated yield was 87% of theory.

Example 10

Fluorination of Chlorobenzene on Ni—Cr Catalyst Supported on $AlF_3$.

In Arkema's EP2665692 (2011) the Ni—Cr catalyst supported on $AlF_3$ is used for the production of 1234yf and applied at 230° C. according to example 1 of this invention. The conversion of chlorobenzene with this catalyst was 56%, the achieved selectivity to fluorobenzene was 94%.

Example 11

Simplified Cr-base fluorination catalyst preparation procedure with $Cr(NO_3)_3$ and ammonia and the application in preparation of fluorobenzene.

An aqueous solution of chromium nitrate and aqueous ammonia were slowly mixed in a Hastelloy C4 vessel and dry ice condenser. The precipitated material was collected and the chromium hydroxide heated to 250° C. The catalyst was pressed into pellets, filed in a Ni-tube and fluorinated with HF 100% (2 h). The application of this catalyst according to example 1 gives 79% conversion of Chlorobenzene, a selectivity to fluorobenzene of 97% and a yield of 94%.

Example 12

Preparation of a Cr—Mg—C-Catalyst and Application Thereof in the Preparation of Fluorobenzene.

Preparation Procedure of a of a Cr—Mg—C Catalyst:

200 g $Cr(NO_3)\times 9H_2O$ were dissolved in 1 l deionized water, then 500 g MgO and 240 g graphite were added and mixed properly. Cutting the cake into small (0.5 cm×0.5 cm parts) and drying at 100° C. until no water leaves the material gives around 1 kg catalyst.

Prefluorination and Conditioning with HF:

The catalyst was filled into a Ni-tube (after a vaporizer and connected to a condenser with reservoir afterwards) of 120 cm length and a diameter of 5 cm. 100% HF was fed through the catalyst bed over 5 h first with 200 g/h, after 2 h with 500 g/h at 250° C.

Conversion of Chlorobenzene to Fluorbenzene:

The reactor temperature was lowered to 230° C. and chlorobenzene feed (over a vaporizer with 180° C.) was adjusted to 300 g/h (15.0 mol) HF and 563 g (5.0 mol) chlorobenzene, both fed over the vaporizer (operated at 180° C. for 1 h) into the Ni-tube reactor. A carefully hydrolyzed sample during the reaction showed almost quantitative conversion of chlorobenzene.

All material collected in the reservoir of the condenser was very carefully fed into ice water and the organic phase carefully distilled at atmospheric pressure in a distillation apparatus out of plas-tics to get 99.9% pure fluorobenzene at 85° C. transition temperature. The isolated yield was 858 g fluorobenzene (89% of theory).

What is claimed is:

1. A process for the manufacture of a fluorinated benzene, in a vapor-phase fluorination process comprising the steps of:
   a) provision of a chlorinated benzene as starting compound;
   b) provision of a fluorination gas consisting of anhydrous hydrogen fluoride (HF);
   c) provision of a fluorination catalyst;
   d) provision of a reactor system, resistant to hydrogen fluoride (HF), and comprising a vaporizer for the starting compound of a), and a condenser for the vapor-phase fluorination reaction product, and a reservoir for collecting the fluorination reaction product;
   e) at least one vapor-phase reaction stage comprising reacting of a) a vaporized chlorinated benzene with b) anhydrous hydrogen fluoride (HF) in gas phase in the presence of c) the fluorination catalyst, so as to produce a vapor-phase fluorination reaction product;
   f) withdrawing the vapor-phase fluorination reaction product formed in the vapor-phase reaction step e) from the reactor or reactor system of d), and transferring the vapor-phase fluorination reaction product to the condenser and condensing for collecting the condensed fluorination reaction product; and
   g) hydrolysing the fluorination reaction product obtained and collected according to f), in water, to obtain a fluorinated benzene; and
   h) phase separation of the organic phase of fluorinated benzene, from water phase to obtain fluorinated benzene
   wherein the fluorination catalyst is selected from the group consisting of $MgF_2$ based catalyst, $SbCl_5/C$ based catalyst, $Cr_2O_3$ based catalyst, and $FeCl_3/C$ based catalyst, and wherein the said catalyst is pre-fluorinated with hydrogen fluoride (HF).

2. The process for the manufacture of a fluorinated benzene according to claim 1, wherein the $Cr_2O_3$ based catalyst is an activated and/or re-activated $Cr_2O_3$ based catalyst.

3. The process for the manufacture of a fluorinated benzene according to claim 2, wherein the activated and/or re-activated $Cr_2O_3$ based catalyst is activated and/or re-activated by treatment with an oxygen containing gas; and/or wherein the $Cr_2O_3$ based catalyst is pre-fluorinated with hydrogen fluoride (HF).

4. The process for the manufacture of a fluorinated benzene according to claim 2, wherein the activated and/or re-activated $Cr_2O_3$ based catalyst is activated and/or re-activated by treatment with Zn dopant, by treatment with Ni dopant.

5. The process for the manufacture of a fluorinated benzene according to claim 4, wherein the activated and/or re-activated $Cr_2O_3$ based catalyst is activated and/or re-activated by treatment with Ni dopant, and wherein the said Ni dopant activated and/or re-activated $Cr_2O_3$ based catalyst is supported on $AlF_3$ as a carrier.

6. The process for the manufacture of a fluorinated benzene according to claim 2, wherein the activated and/or re-activated $Cr_2O_3$ based catalyst is activated and/or re-activated by treatment with Mg dopant, and wherein the said Mg dopant activated and/or re-activated $Cr_2O_3$ based catalyst is additionally treated with carbon (C) to yield an activated and/or re-activated Cr—Mg—C fluorination catalyst.

7. The process for the manufacture of a fluorinated benzene according to claim 1, wherein e) the at least one vapor-phase reaction stage comprising reacting of a) a vaporized chlorinated benzene with b) anhydrous hydrogen fluoride (HF) in gas phase in the presence of c) the fluorination catalyst, so as to produce a vapor-phase fluorination reaction product,
   is performed in a reactor or reactor system of d) which is heated to the reaction temperature of at least about 200° C.; and then the feed into the reactor or reactor system of d), of hydrogen fluoride (HF) feed and halogenated benzene feed, is adjusted in relation to the employed kg-scale quantity of the fluorination catalyst of c), based on 1 kg of the fluorination catalyst, such that the said feed is adjusted to about 3.33 mol/h (0.667 kg/h) HF and about 1.11 mol/h halogenated benzene (about 0.125 kg/h based on chlorobenzene), both feeds fed over the vaporizer, which is operated at 180° C., and based on an operation period of the vaporizer of 1 h.

8. The process for the manufacture of a fluorinated benzene according to claim 1, wherein the fluorinated benzene is monofluorobenzene.

9. The process for the manufacture of a fluorinated benzene according to claim 1, further comprise i) purifying the fluorinated benzene, obtained in h) by distillation under atmospheric pressure to obtain purified fluorinated benzene.

10. The process for the manufacture of a fluorinated benzene according to claim 7, wherein the reaction temperature is at least about 250° C.

11. The process for the manufacture of a fluorinated benzene according to claim 10, wherein the reaction temperature is at least about 280° C.

12. The process for the manufacture of a fluorinated benzene according to claim 7, wherein the halogenated benzene feed is monochlorobenzene (chlorobenzene) feed.

\* \* \* \* \*